United States Patent [19]

Petibon

[11] Patent Number: 4,816,490
[45] Date of Patent: Mar. 28, 1989

[54] NOVEL THERAPEUTIC USE OF A DERIVATIVE OF INDANE DIONE AND THE PHARMACEUTICAL COMPOSITIONS INTENDED FOR THIS USE

[75] Inventor: Guy Petibon, Boulogne Billancourt, France

[73] Assignee: Jouveinal S.A., Paris, France

[21] Appl. No.: 133,949

[22] Filed: Dec. 17, 1987

Related U.S. Application Data

[63] Continuation of Ser. No. 783,935, Sep. 26, 1985, abandoned.

[51] Int. Cl.$^4$ .............................................. A61K 31/12
[52] U.S. Cl. ...................................... 514/681; 514/824
[58] Field of Search ........................ 514/681, 684, 824

[56] References Cited

U.S. PATENT DOCUMENTS 4,395,417 7/1983 Hall et al. ............................ 514/681

FOREIGN PATENT DOCUMENTS 2382424 11/1978 France ................................ 514/684

Primary Examiner—Leonard Schenkman
Assistant Examiner—Joseph A. Lipovsky
Attorney, Agent, or Firm—Bierman and Muserlian

[57] ABSTRACT

A method of reducing hyperlipemia in warm-blooded animals by administration of an effective amount of 2-[(3,4-dimethoxy-benzoyl)-methyl]-2-hydroxy-1,3-dioxoIndone.

3 Claims, No Drawings

NOVEL THERAPEUTIC USE OF A DERIVATIVE OF INDANE DIONE AND THE PHARMACEUTICAL COMPOSITIONS INTENDED FOR THIS USE

This application is a continuation of U.S. patent application Ser. No. 783,935 filed Sept. 26, 1985 which is now abandoned.

THE INVENTION

This invention relates to a novel therapeutic use of a derivative of Indanedione and to the pharmaceutical compositions to be utilized for such therapeutic use.

More particularly this invention relates to the use as a normolipaemiant drug of a compound resulting from the reaction of Ninhydrin with an Acetophenone and specifically this invention provides the use as a normolipaemiant drug, 2-[(3,4-dimethoxy-benzoyl)-methyl]-2-hydroxy-1,3-dioxo Indane. By normolipaemiant drug is meant a compound which permits the return to normality of pathological biological parameters connected with hyperlipemia.

The said compound has the following structural formula

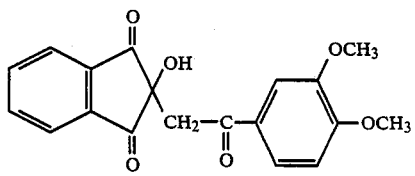

It has already been disclosed in French Pat. No. 2,382,424 wherein it has been broadly claimed in a generic claim which includes it. In the said French patent, it is also disclosed as industrial use that the claimed compounds of the generic formula have valuable therapeutic properties, namely anti-inflammatory, analgesic and spasmolytic properties.

This invention provides a novel therapeutic use for one of the compounds encompassed by the generic formula of the said French patent and more precisely the use as an antilipaemiant agent of 2-[(3,4-dimethoxy-benzoyl)-methyl]-2-hydroxy-1,3-dioxo-Indane. These novel therapeutic properties seem quite surprising due to the fact it appears unusual that an anti-inflammatory or analgesic or spasmolytic drug shows such therapeutic properties. This invention appears even more surprising as the activity is evidenced at doses lower than previously disclosed and where the said compound does not show anti-inflammatory or analgesic properties.

The said 2-[(3,4-dimethoxy-benzoyl)-methyl]-2-hydroxy-1,3-dioxo-Indane has been used in the French patent at a dose of 250 mg/kg to induce an anti-inflammatory threshold effect. Consequently, the dosology disclosed in the French patent for the use in human therapy shall range from 400 to 1200 mg daily.

More recently it has been evidenced that 2-[(3,4-dimethoxy-benzoyl)-methoxy]-2-hydroxy-1,3-dioxo-Indane from a dose of 100 mg/kg shows a clear antilipaemiant activity and that in a very severe test as the hyperlipaemia caused by TRITON WR 1339 in the rats, the hyperlipaemia was antagonized or decreased from an oral dose of 125 mg/kg. Moreover, the said compound shows a very low toxicity and the administration thereof may be made at higher dosages without any risk of toxic side-effects or for very protracted sets of time.

The normolipaemiant activity of 2-[(3,4-dimethoxy-benzoyl)-methyl]-2-hydroxy-1,3-dioxo-Indane is ascertained also by the biochemical blood level (total cholesterol blood esterified cholesterol, HDL level, LDL level, blood total lipids, blood triglycerids) and by the histological improvement. Macroscopic examinations performed on animals made atheromatic with a diet rich in cholesterol show in the animals receiving at the same time the compound of the invention, a lower frequency of macroscopic damages, hence a lower percentage of damaged animals and a lower intensity of the observed damages. In these tests, the compound of the invention has been compared to Clofibrate and Fenclofibrate given at the same doses and 2-[(3,4-dimethoxy-benzoyl)-methyl]-2-hydroxy-1,3-dioxo-Indane appears to be as active as Clofibrate on the biochemical level and more active when evaluating the macroscopic damages.

Further, this invention provides pharmaceutical compositions intended to treat hyperlipidaemia, hypercholesterolaemia and atheromatosis, characterized in that they include from 50 to 200 mg of active ingredient per unit dosage. In a preferred manner, the pharmaceutical compositions of the invention include from 100 to 200 mg of 2-[(3,4-dimethoxy-benzoyl)-methyl]-2-hydroxy-1,3-dioxo-Indane in admixture or in conjunction with an inert, non-toxic, pharmaceutical acceptable carrier or vehicle. The daily dosage in the adult ranges from 300 to 600 mg divided into 3 to 6 administrations.

The pharmaceutical compositions of the invention are those suitable for administration parenterally, orally or rectally. For this purpose, they may be in the form of coated or uncoated tablets, dragees, capsules, tablets to be divided or not, multilayer tablets, tablets with sustained release, micro capsules with enteric coating, soft capsules, soft gelatine capsules, pills, cachets, drinkable solutions or suspensions, injectable solutions or suppositories.

The following examples illustrate the invention. It does not limit it in any manner.

EXAMPLE 1

Toxicological studies of 2-[(3,4-dimethoxy-benzoyl-methyl]-2-hydroxy-1,3-dioxo-Indane

1. METHOD 1.1 Animals

Male and female mice of Swiss strain weighing from 22 to 25 g of body weight were free of pathogen specific organisms (EOPS), stemming from breeding CERJ (53860 LE GENEST (France) and acclimated for at least 8 days in the animalry of the firm.

1.2 Housing conditions

Except where stipulated to the contrary, in the tables giving the results, 10 animals of the same sex for each dose were housed in cages of MAKROLON (Safi) of 40 cm by 25 cm filled with shaving of wood. Standard feeding for rats and mice, tablets UAR and tap water ad libitum.

1.3 Treatments

The compounds were administered without previous fasting either orally (gastric tubing using a metallic oesophageous sonde) at a rate of 0.5 ml or 1 ml per 20 g of body weight of an aqueous suspension of the test compound in a 3% solution of arabic gum, or intraperitoneally at a rate of 0.5 ml or 1 ml per 20 g of body weight of the test compound suspended in an isotonic saline solution containing 3% of arabic gum.

1.4 Survey of the animals was effected

For 6 days after the single administration and then every day for 15 days.

1.5 Calculation of the results

When necessary, the mean lethal doses (LD 50) were calculated by the method of Behrens and Karber (BK) and Miller and Tainter (MT). The latter allowing to supply with, for the threshold of probability $P=0.05$ a limit of confidence for the LD 50. Further calculated were the LDo i.e. DMT=maximal doses always tolerated and the LD100 i.e. DMM=minimal doses always lethal.

2. RESULTS 2.1 Intraperitoneally

| Compound in mg/kg IP | Administered volume in ml/20 g | Concentrations in parts/100 | Mortality in 10 mice males | females |
|---|---|---|---|---|
| 2000 | 0.5 | 8 | 0 | 0 |
| 2500 | 0.5 | 10 | 1 | 1 |
| 3000 | 0.5 | 12 | 3 | 6 |
| 3500 | 0.5 | 14 | 5 | 8 |
| 4000 | 0.5 | 16 | 8 | 10 |
| 4500 | 0.5 | 18 | 10 | 10 |
| 5000 | 0.5 | 20 | 10 | 10 |

| | Male Mice | Female Mice |
|---|---|---|
| LDo = | 2000 mg/kg | 2000 mg/kg |
| LD50 = | 3400 mg/kg (BK) | 3000 mg/kg (BK) |
|  | 3350 mg/kg ± 100 mg/kg (MT) | 3000 mg/kg ± 145 mg/kg (MT) |
| LD100 = | 4500 mg/kg | 4000 mg/kg |

Mortality and symptoms

The mortalities were not immediate and occurred from 24 to 48 hours after the injection. For the moderate doses (from 3 to 4 g/kg per day), it had also been reported some mortalities after 5 to 7 days, generally 1 death per dose for each sex. The initial symptoms shown were crawling after the injection then a protracted prostation took place with piloerection and bradypnea cyanosis. The death occurred after respiration arrest in 24 to 48 hours. The surviving micr remained prostrate for about a week, at least at a dose which induced some deaths.

2.2 Orally

The compound was administered in a single dose to batches of 10 male or female mice weighing 10 g/kg at a rate of 1 ml per 20 g of body weight. At this oral dose of 10 g/kg, no deaths nor toxic symptoms appeared.

LDo 10 g/kg

LD50 and LD100>10 g/kg

3. CONCLUSIONS

The studies on the toxicity after single administration (i.e. acute toxicity) of the test compound have been carried out on male and female mice orally and intraperitoneally in comparison with Clofibrate. Orally, the test compound had no toxicity even at a dose of 10 g/kg while Clofibrate had the following LD 50: 2500 mg/kg 2500 mg/kg±235 mg/kg for male mice 2650 mg/kg±190 mg/kg female mice Intraperitoneally, the test compound was markedly less toxic than Clofibrate since the calculated LD 50 were about:

3000 mg/kg for the test compound 1800 mg/kg for male mice 1700 mg/kg for female mice/for Clofibrate Conclusively, the test compound was less toxic than Clofibrate after a single administration either orally or parenterally.

EXAMPLE II

Studies on the hypolipaemiant activity of 2-[(3,4-dimethoxy-benzoyl)-methyl]-2-hydroxy-1,3-dioxo-Indane

1. METHOD

Hyperlipidaemia in the rate of the (Wistar strain induced by injection of TRITON WR 1339 was antagonized or decreased by administrating hypolipaemiant agents

2. TECHNIQUE (a) General conditions of the tests

Male Wistar Rats

Body weight: 150–180 g

Germ free animals (EOPS)

Feeding by standard Regimen UAR A04

Drinking water ad libitum 6 animals per dose in a cage in MAKROLON of 60×40 cm filled with shavings of wood.

Cages placed in an animalry at constant temperature (19° to 20° C.), constant humidity of 40 to 60%, replacement of the air 10 times per hour and enlightened for 12 hours per day.

(b) Performance of the tests 18 hours before: fasting of the animals

TO: administration of TRITON WR 1339 (400 mg/kg IP)

10 mn after: administration of the test compound 6 hours after: 1st sampling of the blood at the retro-orbital sinus 24 hours after: 2nd sampling of the blood at the retro-orbital sinus Batches for the treatment Each test included 8 batches of which one was a control (healthy animals) and one was a control with Triton WR 1339-treated animals.

TABLE I

| Batch | Compound | Doses in mg/kg | Way | Number of animals |
|---|---|---|---|---|
| 1 | Controls | — | — | 6 |
| 2 | Controls with Triton WR 1339 | — | — | 9 |
| 3 | Compound according to the invention | 125 | oral | 6 |
| 4 | — | 250 | oral | 12 |
| 5 | — | 250 | oral | 6 |
| 6 | — | 750 | oral | 6 |
| 7 | Procetofene | 250 | oral | 12 |
| 8 | Procetofene | 500 | oral | 6 |

The sum of individual scores of each of the surviving animals at the end of the treatment allowed the calculation of the activity for the various compounds in relation with the results obtained with the controls and with Procetofene.

3. BIOLOGICAL TESTING 6 and 24 hours after intraperitoneal administration of TRITON WR 1339, the following testing was carried out:

Total cholesterol by the colorimetric method of RICHMOND

Cholesterol in HDL by the colorimetric method of RICHMOND after precipitation by CONCANAVALIN A Cholesterol in LDL by the colorimetric method of RICHMOND after precipitation by CONCANAVALIN A Total lipids by the Zollner's sulphophosphovanillic method Triglycerids by the BUCOLO's enzymatic method.

4. RESULTS

The individual results of the blood samplings performed 6 hours and 24 hours after, were the results in percentage in comparison to those obtained with 250 mg/kg of Procetofene and they are reported in Tables II and III.

TABLE II

| Test compounds, scores compared to those of 250 mg/kg Procetofene - 6 hours after | | | | | |
|---|---|---|---|---|---|
| Compound | doses in mg/kg | Cholesterol Total | Lipids Total | Triglycerids | Cholesterol HDL/LDL | Total Score |
| Compound according to the invention | 125 | 2.44 | — | 0.31 | — | 2.75 |
| Compound according to the invention | 250 | 1.15 | 0.92 | 0.80 | 0.87 | 3.74 |
| Compound according to the invention | 500 | 0.35 | 1.00 | 1.60 | 2.00 | 4.95 |
| Compound according to the invention | 750 | 0.78 | 0.14 | 0.80 | — | 1.72 |
| Procetofene | 250 | 1.00 | 1.00 | 1.00 | 1.00 | 4.00 |
| Procetofene | 500 | 1.65 | 0.65 | 1.29 | 1.53 | 5.12 |

TABLE III

| Test compounds, score in comparison with 250 mg/kg Procetofene - 24 hours after | | | | | |
|---|---|---|---|---|---|
| Compound | doses in mg/kg | Cholesterol Total | Lipids Total | Triglycerids | Cholesterol HDL/LDL | Total Score |
| Compound according to the invention | 125 | 0.28 | — | 0.26 | 1.40 | 1.94 |
| Compound according to the invention | 250 | 1.13 | 1.56 | 0.85 | 1.10 | 4.64 |
| Compound according to the invention | 500 | 0.75 | 1.62 | 0.49 | 0.80 | 3.66 |
| Compound according to the invention | 750 | 0.61 | — | 0.72 | 0.40 | 1.73 |
| Procetofene | 250 | 1.00 | 1.00 | 1.00 | 1.00 | 4.00 |
| Procetofene | 500 | 1.17 | 0.85 | 1.01 | 0.30 | 3.33 |

5. CONCLUSIONS

The hypolipaemiant activity of the compound of the invention has been studied against the hyperlipidemia induced by TRITON WR 1339 in the Wistar male rat in comparison with that of Procetofene. At the tested doses (250 and 500 mg/kg), the activity of both drugs was directly proportional to the doses, 6 hours after intoxication by TRITON WR 1339 and inversely proportional to the dose 24 hours after. At the same doses, the compounds show an antihyperlipaemiant activity about equal against the noxious effect of TRITON WR 1339.

EXAMPLE III

Hypolipaemiant and antitheromatous activities of 2-[(3,4-dimethoxy-benzoyl)-methyl]-2-hydroxy-1,3-dioxo-Indane

1. METHOD

The method utilized for the test was that, slightly altered of Aubert D. Feraud J. C., Lacaze B., Pepino., Ponak E. et Podesta M. as described in Atherosclerosis, Vol. 20 (1974), p. 263–280 (Experimental Atherogenesis in the Wistar Rat).

2. Main features of this test
    (a) Animals-diet

Female rats of Wistar strain, free of specific pathogenic germs (EOPS) stemming from the breeding EVIC-CEBA Mean body weight: 160–180 g at the start of the test Diet: standard tablets UAE AO 3 enriched in cholesterol (0.5%) and in cholic acid (0.5).

Drinking water: tap water 15 animals per each batch and by cage in MACROLON (Safi) of 59 cm × 38 cm, 5 cm filled with a litter of shavings of wood.

Cages housed in a special room at constant temperature (20±1° C.), at constant humidity (50%±10%).

Duration of the enlightening: 12 hours per day (from 7 hour a.m. to 7 hour p.m.).

Diet of the animals: the animals were given the atheromatogenous regimen then while maintaining the same regimen, they were given for 4 days 250,000 IU/kg of vitamin $D_2$ dissolved in olive oil (Sterogyl 15H). The compounds to be tested were given thereafter for 4 weeks immediately after the termination of the atheromatogenous regimen.

(b) Batches of animals for the treatment

TABLE IV

| Batch | Treatment |
|---|---|
| 1 | Controls |
| 2 | Animals submitted to the atheromatogenous regimen |
| 3 | Fenclofibrate at 100 mg/kg |
| 4 | Clofibrate at 100 mg/kg |
| 5 | Compound of the invention at 100 mg/kg |

(C) Remarks

The behavior and the changes in weight of the animals were surveyed every day as well as by weekly weighing. The studies on the evolution of the body weight did not show any significant variation between the various batches and this was an indication of a good tolerance of the treatment. Mortality was noticed for each batch and it could reach 30% of the animals and hence at least 15 animals per batch were needed. The chronic administration of 100 mg/kg of Clofibrate corresponded to the maximal-tolerated dose in the healthy rat according to the experiments performed in our laboratories. Under these experimental conditions, Clofibrate (4/15) and Fenclofibrate (3/15) increased the mortality level while the compound of the invention did not increase it in comparison with that of batch No. 2 (2/15).

3. Histopathology

The aorta, livers, hearts of the rats after sacrifice were stained with an aqueous solution of Bouin's Reagent and embedded in paraffin after washing with alcohols at increasing concentration and with toluene. The hearts were kept in blocks of paraffin for a further examination when necessary. The livers were stained using the technique of Hematein-eosin and the aorta were stained using the techniques of orcein-light green to evidence the structural damages of the elastic strips periodic acid, then Schiff's Reagent to locate the deposits of mucopolysaccharids Hematein, then Esoin to evidence the deposits of calcium.

The intensity of the observed damages and the degree of atheromatosis were determined using one of the following scores:

|  | Score |
|---|---|
| no atheromatosis | 0 |
| ± very slight level of atheromatosis | 0.5 |
| slight level of atheromatosis | 1 |
| Moderate level of atheromatosis | 2 |
| significant level of atheromatosis | 3 |

The areas of atheroma were numbered on an identical length for each of the examined aortas. It has to be noted that as the word atheromateous area was concerned, it included from the small damages (break of at least three elastic strings, the ends of which are separated by a space invaded by a Mac Manus-positive substance or optionally calcified) to the more extended damages.

4. Biochemical Testings

At the end of these studies the following tests were performed on all surviving animals.
Total blood cholesterol
Esterified blood cholesterol
Cholesterol in HDL
Cholesterol in LDL (estimate)
Total blood lipids
Blood triglycerids 5. Necropsy After the studies, all the animals were sacrificed by subtotal puncture of the blood in the abdominal aorta after anesthesia by intravenous sodium Pentobarbital. The hearts, livers, aortas on which the score of atheroma was determined were taken. For this purpose, the aortas were longitudinally cut, then spread to allow a whole insight of the endothelial coating from the aortic valves until the branching of the coeliac stem (lower portion of the thoracic aorta).

Aorta was from an anatomic point of view divided into two parts:

Zone 1: aortic valves-first intercostal arters

Zone 2: first intercostal arters and branching of the coeliac stem

The intensity of the atheromatous deposits was determined according to the following scores:
Score 0: No deposit
Score 1: Discrete (<1 mm) and few deposit
Score 2: Numerous and discrete deposits
Score 3: Numerous and marked deposits (<1 mm)
Score 4: Very marked deposits or very numerous deposits but letting some uninfiltrated areas
Score 5: Deposits on the whole epithelium 6. Results The results based on these studies allowed the following classification of the anti-atheromatous action of the tested products. Compound of the invention>Fenofibrate>Clofibrate.

Biochemical Test

The results of the biochemical tests were reported in the Tables. Table V shows the percentage of variation in comparison with the controls-diet (batch 2) and gives the score obtained by the product for each studied parameter in comparison with those of Clofibrate (Clofibrate=1). The total score for each product was obtained by adding each individual scores and allowed the following classification Clofibrate (6)>compound of the invention
(5.6)>Fenclofibrate (1.98)

The protection against the atheromatogenous risk was evaluated using the following ratios:

TABLE VI $$\frac{\text{Total blood cholesterol}}{\text{Cholesterol in HDL}}$$

and $$\frac{\text{Cholesterol in LDL}}{\text{Cholesterol in HDL}}$$

The classification for each of the compounds was based on these ratios, as follows:

Colifibrate (2)>Compound of the invention
(0.9)>Fenclofibrate (0.23)

Macroscopic examinations (TABLE VII)

Two parameters were considered:
the number of animals showing macroscopic damages and hence the percentage of damaged animals
the intensity of the observed damages determined according to the previously-given scores.

The classification for each compound was as follows:

Compound of the invention (2.57)>Fenclofibrate
(2.17)>Clofibrate (2)

Histopathological examinations

The histopathological examinations provided individual scores which were analyzed, then reported for each batch. Three parameters were distinctly determined:

1. The number of animals showing histopathological damages, hence the percentage of damaged animals. This percentage may be different from that macroscopically found since the histological slices may avoid or may include some areas which were seen from the macroscopical examination. In contrast, some areas which could be seen by the histological examination may not be seen during the macroscopical examination.

2. The intensity of the atheromatous damages found, determined by the previously-given scores.

3. The number of the observed atheromatous damage calculated on the basis of a batch of 15 animals each.

The results of these observations allowed the following classification of the compounds:

Fenclofibrate (2.13) > Clofibrate (2.00) > Compound of the invention (1.3).

TABLE VIII

| | Scores | | Compound of this invention |
|---|---|---|---|
| | Fenclofibrate | Clofibrate | |
| Biochemistry | 1.98 | 6.00 | 5.67 |
| Atheromatous risk | 0.23 | 2.00 | 0.90 |
| Macroscopical examination | 2.17 | 2.00 | 2.57 |
| Histological examination | 2.13 | 3.00 | 1.32 |

TABLE V

BIOCHEMICAL TESTINGS
(Percentage of variation in comparison to the animals controls-Diet)

| Batch | Total blood cholesterol % | Score | Esterified cholesterol % | Score | Cholesterol in HDL % | Score | Cholesterol in LDL % | Score | Total Blood lipids % | Score | Triglycerids % | Score |
|---|---|---|---|---|---|---|---|---|---|---|---|---|
| Controls | | | | | | | | | | | | |
| Controls-Diet | | | | | | | | | | | | |
| Fenclofibrate | −1.09 | 0.02 | −22.08 | 0.40 | +4.17 | 0.04 | −8.69 | 0.16 | −10.31 | 0.29 | −25.86 | 1.07 |
| Clofibrate | −48.75 | 1.00 | −55.00 | 1.00 | +104.17 | 1.00 | −55.37 | 1.00 | −35.43 | 1.00 | −24.14 | 1.00 |
| Compound according to this invention | −55.47 | 1.14 | −57.70 | 1.05 | −33.33 | — | −57.41 | 1.04 | −48.47 | 1.37 | −25.86 | 1.07 |

TABLE VI

RISK OF ATHEROMA

| Batch | Total Blood Cholesterol Score | % in comparison with Controls-Diet | Cholesterol in HDL Score in comparison with Clofibrate (=1) | Score | Cholesterol in LDL % in comparison with Controls-Diet | Cholesterol in HDL Score in comparison with Clofibrate | Total Score |
|---|---|---|---|---|---|---|---|
| Controls | 7.28 | | | 5.07 | | | |
| Controls Diet | 26.67 | | | 24.46 | | | |
| Fenclofibrate | 25.32 | −5.06 | 0.07 | 21.44 | −12.35 | 0.16 | 0.23 |
| Clofibrate | 6.69 | −74.91 | 1.00 | 5.35 | −78.13 | 1.00 | 2.00 |
| Compound according to this invention | 17.81 | −33.22 | 0.44 | 15.63 | −36.10 | 0.46 | 0.90 |

TABLE VII

Macroscopical Examinations

| Batch | Damaged animals Percentage | % of decrease in comparison with Controls-Diet | Score in relation to Clofibrate | Quotation | Intensity of the damages % of decrease in comparsion with Controls-Diet | Score in relation to Clofibrate | Total scores |
|---|---|---|---|---|---|---|---|
| Controls | 0 | — | — | — | — | — | — |
| Controls-Diet | 100 | — | — | 2.69 | — | — | — |
| Fenclofibrate | 83.33 | −16.67 | 0.92 | 1.83 | −31.97 | 1.25 | 2.17 |
| Clofibrate | 81.82 | −18.18 | 1.00 | 2.00 | −25.65 | 1.00 | 2.00 |
| Compound according to this invention | 69.23 | −30.77 | 1.69 | 2.08 | −22.68 | 0.88 | 2.57 |

| Total Score | 6.51 | 13.00 | 10.46 |
|---|---|---|---|

7. CONCLUSIONS

After having studied the hypolipaemiant activity and the anti-atheromatous activity of the compound of the invention using a diet according to Aubert (loc. cit.) slightly modified, in comparison with that of Clofibrate and of Fenclofibrate, it can be concluded that 100 mg/kg of Clofibrate is about the maximal dose well tolerated for the rat in protracted administration. At the same dose, the compound of the invention is better tolerated. The total scores obtained for the various compounds tested are summarized in Table VIII.

Under the experimental conditions used, the compound of the invention at a dose of 100 mg/kg showed marked hypolipaemiant and anti-atheromatous activity, very close to Clofibrate (100 mg/kg) and far better than those of Fenclofibrate (100 mg/kg).

What is claimed is:

1. A method of reducing hyperlipemia in hyperlipimic warm-blooded animals comprising administering to hyperlipimic warm-blooded animals an antihyperlipemically effective amount of 2-[(3,4-dimethoxy-benzoyl)-methyl]-2-hydroxy-1,3-dioxoindane as the active compound.

2. The method of claim 1 wherein the daily dose of the active compound is 300 to 600 mg/kg.

3. The method of claim 2 wherein the dose is administered 3 to 6 times a day.

* * * * *